United States Patent [19]

Mazurik et al.

[11] Patent Number: 5,135,512
[45] Date of Patent: Aug. 4, 1992

[54] DISPOSABLE SYRINGE FOR INJECTIONS

[76] Inventors: Sergei M. Mazurik, ulita Lenina, 92, kv.57, Poltava, U.S.S.R.; Oleg V. Efremov, ulitsa 60-let Oktyabrya,3, kv.58, Poltavskaya oblast Karlovka, U.S.S.R.

[21] Appl. No.: 670,426

[22] Filed: Mar. 18, 1991

Related U.S. Application Data

[63] Continuation of Ser. No. 000,259, Sep. 28, 1989, abandoned.

[30] Foreign Application Priority Data

May 16, 1989 [SU] U.S.S.R. ............................. 4684319

[51] Int. Cl.$^5$ ............................................. A61M 5/315
[52] U.S. Cl. ..................................... 604/228; 604/110
[58] Field of Search ............... 604/110, 218, 221, 222, 604/228

[56] References Cited

U.S. PATENT DOCUMENTS 4,973,308  11/1990  Borras et al. ..................... 604/110

FOREIGN PATENT DOCUMENTS

| 0304386 | 2/1989 | European Pat. Off. | 604/110 |
| 0325886 | 8/1989 | European Pat. Off. | 604/110 |
| 2205750 | 12/1988 | United Kingdom | 604/110 |
| 8906146 | 7/1989 | World Int. Prop. O. | 604/110 |
| 8909074 | 10/1989 | World Int. Prop. O. | 604/110 |
| 9012612 | 11/1990 | World Int. Prop. O. | 604/110 |

*Primary Examiner*—C. Fred Rosenbaum
*Assistant Examiner*—Sharon Finkel
*Attorney, Agent, or Firm*—Beveridge, DeGrandi & Weilacher

[57] ABSTRACT

A disposable syringe for injections comprises a cylindrical housing (1), which accommodates a piston (5) with a rod (6), and a needle fixing device (4). The piston (5) and the rod (6) are mechanically disengaged from each other, a flange (7) is provided at the end of the rod (6), and a washer (8) is fitted on the rod (6) coaxially therewith. The diameter of the hole in the washer (8) is smaller than the diameter of the flange (7), while the outside diameter of the washer (8) exceeds the inside diameter of the housing (1) by such an amount that the force of friction between the outer surface of the washer (8) and the inner surface of the housing (1) surpasses the force exerted upon the washer (8) as a result of motion performed by the housing (1), including as accelerated motion thereof. The disposable syringe is equally applicable in any medical institution and for individual use.

5 Claims, 3 Drawing Sheets

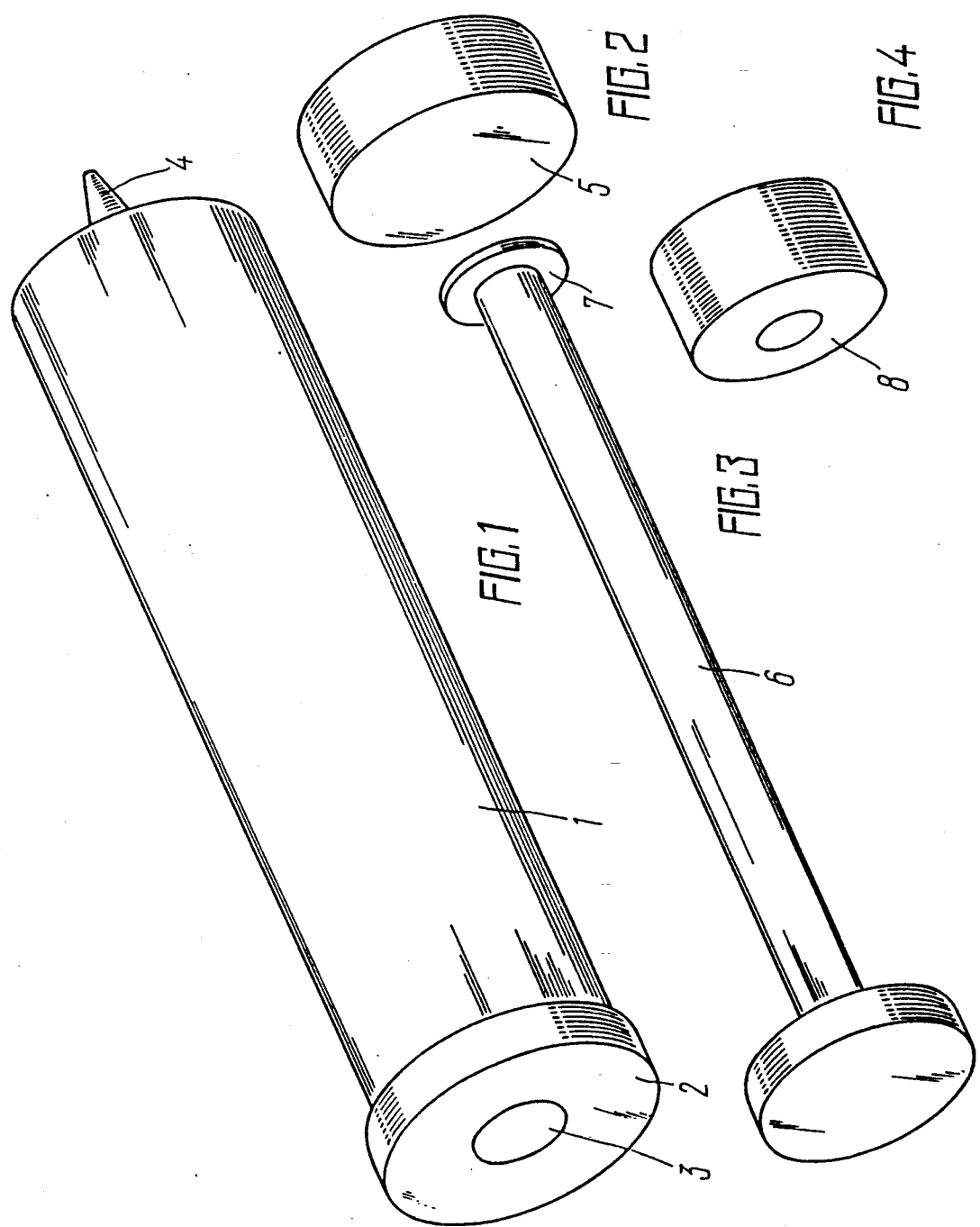

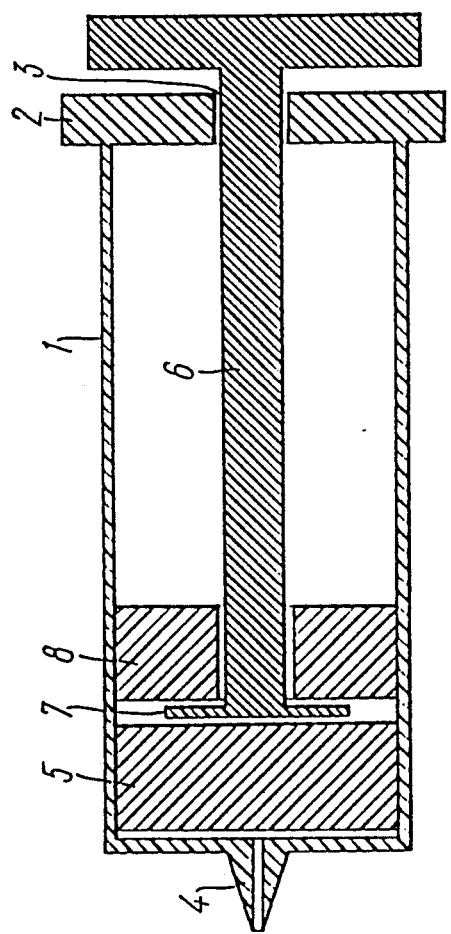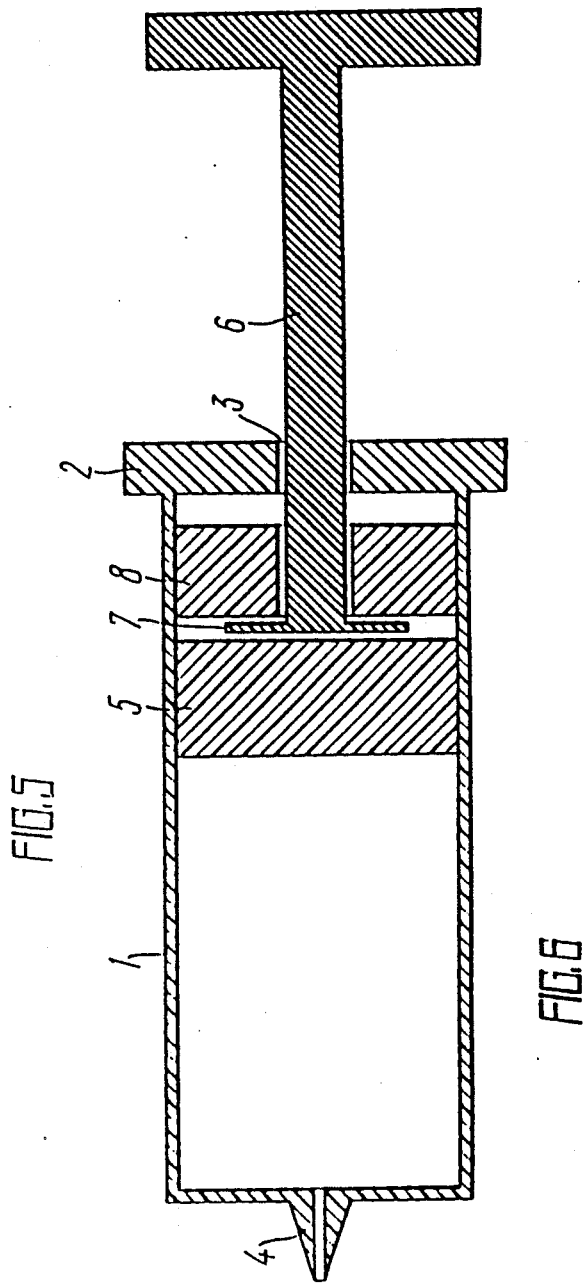

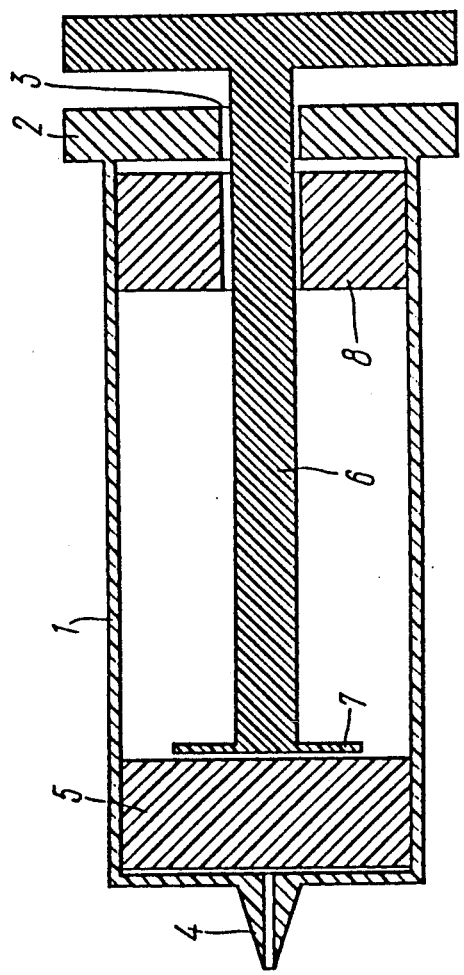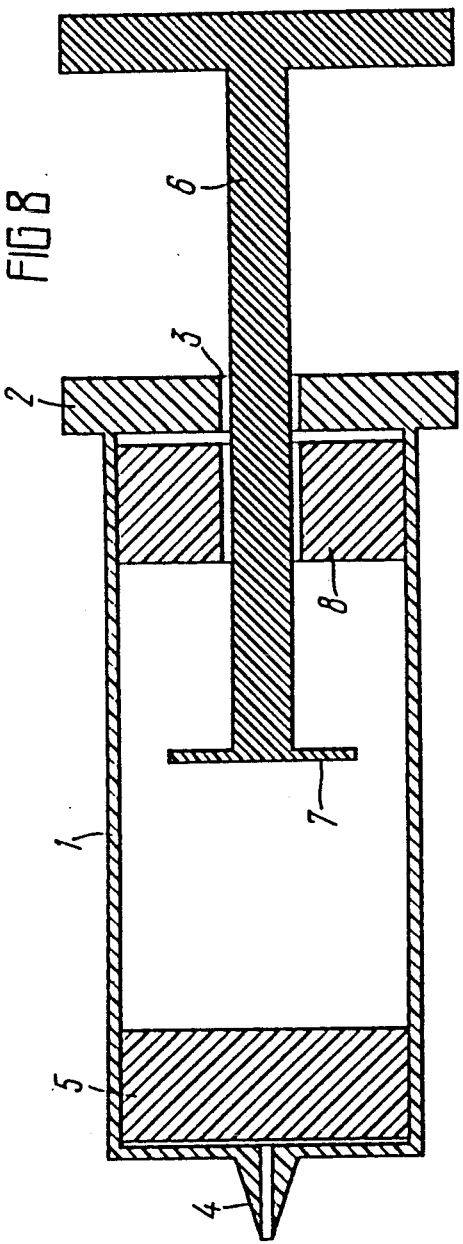

DISPOSABLE SYRINGE FOR INJECTIONS

This application is a continuation of PCT/SU89/00259 which was filed on Sept. 28, 1989 with the United States designated, now abandoned. The contents of the PCT/SU89/00259 application is incorporated herein by reference.

TECHNICAL FIELD

This invention relates generally to medical engineering and, more specifically, to disposable syringes applied for injections.

PRIOR ART

Some disposable syringes for injections known to be in widespread use nowadays comprise a cylindrical housing, a piston with a rod accommodated in said housing, and a needle fixing device (cf., e.g., disposable syringes available from Trumo Europe Co., Belgium). The syringes in question differ very little from disposable syringes now in extensive use in modern medical practice, the sole exception residing in that they are made of a cheaper material (i.e., polymer) and therefore are not subject to sterilization. This means that the construction of the known disposable syringes enables one to make repeated use of them, which may occur on account of inattentive or unscrupulous action of medical staff, or when injections are made by those who are in narcotic or alcoholic intoxication. All situations stated above can prove to be of importance, since such cases are fraught with a danger of infection with the virus of AIDS, that of infectious hepatitis, and of some other diseases.

One more prior-art disposable syringe is known to comprise a cylindrical housing accommodating a piston with a rod, and a needle fixing device (EP, A, 0282097).

The syringe under discussion features its needle fixed in a washer situated in the front portion of the syringe housing and capable of reciprocating lengthwise the axis of the housing. The piston disposed past the washer in the syringe housing and rigidly coupled to the rod is not engaged with the washer but has catches adapted for the piston to engage the washer when both of them interact with each other through their end faces. At the end of the injection when the piston and the washer get in contact with each other through their end faces, the piston becomes engaged rigidly by means of the catches, with the washer, wherein the needle is fixed, with the result that any attempt to repeatedly draw a fresh portion of injection substance in the syringe, the washer together with the needle is entrained by the piston into the housing of the syringe. As soon as the needle gets inside the housing it is offset with respect to the axis of the housing so that any attempt to perform an injection results in breakage of the injection needle.

However, the aforementioned construction leaves room for reusing a syringe, since the piston gets engaged with the washer only when in its fully extended position in the front portion of the housing. This causes the needle to be retracted into the housing, whereby the syringe gets unfit for further use. Should the piston be not brought to the fully extended position during injection, the syringe can be applied for making an unlimited number of injections involving almost complete utilization of the holding capacity of its housing.

DISCLOSURE OF THE INVENTION

It is an object of the invention to provide such a construction of a disposable syringe for injections that would prevent any possibility of reusing such a syringe.

The essence of the invention resides in the fact that in a disposable syringe for injections, comprising a cylindrical housing, which accommodates a piston with a rod, and a needle fixing device, according to the invention, the piston and the rod are mechanically disengaged from each other, the rod diameter is smaller than the piston diameter and the rod end facing the piston has a flange has a flange, a washer being set on the rod coaxially therewith, the diameter of the hole in said washer being smaller than the flange diameter, whereas the outside diameter of the washer exceeds the inside diameter of the housing to such an extent that the force of friction between the inner surface of the washer and the inner surface of the housing surpasses the force exerted on the washer as a result of motion performed by the housing, including an accelerated motion thereof.

The disposable syringe for injection, according to the present invention, makes impossible repeated injections, is simple to manufacture, and reliable in operation. Production costs of such a disposable syringe, according to the invention, do not practically exceed those of the heretofore-known disposable syringes.

SUMMARY OF THE DRAWINGS

In what follows the invention will now be disclosed in a detailed description of a specific exemplary embodiment thereof given by way of illustration with reference to the accompanying drawings, wherein:

FIGS. 1, 2, 3, 4 present a perspective disassembled view of a disposable syringe for injections, according to the invention;

FIG. 5 is a longitudinal sectional view of a disposable syringe for injections, according to the invention, when in an assembled state in the initial position before drawing-in an injection substance;

FIG. 6 is a view of the disposable syringe of FIG. 5 at the instant when an injection substance is drawn in;

FIG. 7 is a view of the disposable syringe of FIG. 5 as shown after injection; and FIG. 8 is a view of the disposable syringe of FIG. 5 while an attempt is made to repeatedly draw in an injection substance.

PREFERRED EMBODIMENT OF THE INVENTION

The disposable syringe for injections comprises a cylindrical housing 1 (FIGS 1, 5) one of whose ends carries a cover 2 held to the housing 1 through an inseparable joint. The cover 2 has a central hole 3. The opposite end of the housing 1 has a needle fixing device made as a cannula 4. The housing 1 accommodates a piston 5 (FIGS. 2, 5 to 8), which rightly closes the cross-sectional area of the cylindrical housing 1.

A rod 6 (FIGS. 3, 5 to 8) is accommodated in the housing 1 in tandem with the piston 5. The rod 6 is mechanically disengaged from the piston 5 and has the diameter smaller than the diameter of the piston 5 and then the diameter of the hole 3 so as to provide free motion of the rod 6 inside the housing 1 through the hole 3 in the cover 2. A flange 7 is provided at the end of the rod 6 which faces the piston 5, and a washer 8 (FIGS. 4 to 8) is fitted on the rod 6 coaxially therewith.

The diameter of the hole in the washer 8 exceeds the diameter of the rod 6 but is smaller than the diameter of the flange 7. The outside diameter of the washer 8 surpasses the inside diameter of the housing 1 to such an extent that the force of friction between the outer side surface of the washer 8 and the inner surface of the housing 1 exceeds the force applied to the washer 8 when the housing 1 moves, including accelerated motions of the latter.

The disposable syringe for injections, according to the invention, is applied as follows.

When in the initial position the piston 5 is situated in the front end portion of the housing 1 of the syringe that carries the cannula 4 (FIG. 5). The rod 6 adjoins the piston 5 through the surface of the flange 7, while the washer 8 rests against the flange 7. To draw in an injection substance the rod 6 is extended from the housing 1 of the syringe through the hole 3. As a result, the flange 7 of the rod 6 gets tightly pressed against the washer 8, thus hermetically sealing the space confined within the rod 6 with the washer 8 on the one side, and the piston 5, on the other side, which in turn provides for travel of the piston 5 after the rod 6 and the washer 8 throughout the pathway of the rod 6 when drawing in an injection substance (FIG. 6). To perform injection the rod 6 is to be moved in a reverse direction, i.e., to be retracted into the housing 1 of the syringe, thereby causing the piston 5 (FIG. 7) to move towards the front end of the housing 1. In this case the washer 8 remains in the rear end portion of the housing 1 of the syringe, i.e., nearby the cover 2, which is ensured by virtue of the force of friction between the outer side surface of the washer 8 and the inner surface of the syringe housing 1. The outside diameter of the washer 8 is so selected that the force of friction between the outer side surface of the washer 8 and the inner surface of the syringe housing 1 be substantially in excess of the force exerted upon the washer 8 when the syringe housing performs axial accelerated motions. This in turn rules out a possibility of returning the washer 8 to the initial position when the piston 5 travels towards the front end of the housing 1. A mechanical return of the washer 8 to the initial position is not practicable either, since the cover 2 is joined to the housing 1 through a permanent joint.

A repeated attempt to draw in an injection substance in the syringe will be futile, since the rod 6 alone, devoid of the washer 8 is incapable of establishing hermetic sealing and rarefaction, which are indispensable for the piston 5 (FIG. 8) to travel.

Thus, only a single use of the syringe is possible, whereupon it is to be discarded and is subject to reclamation.

Widespread application of the disposable syringe, according to the invention, will help practically rule out patient's infection, during injections, with the virus of AIDS, that of infectious hepatitis, and of some other diseases communicable by parenteral administration of medicinal agents.

INDUSTRIAL APPLICABILITY

The invention is applicable is any medical institution and for individual use for subcutaneous, intramuscular and intravascular injections.

What is claimed is:

1. A disposable syringe for injections, comprising:
   a cylindrical housing having a forward end, a rearward end, and an internal surface;
   a needle fixing device extending forwardly from the forward end of said cylinder;
   a cover permanently fixed to the rearward end of said cylinder, said cover including a central hole;
   a rod slidingly received within the central hole, said rod having a first end adapted for movement within said cylinder;
   an end extension member fixed to said first end of said rod, said end extension member having a forward surface and an external periphery which is greater than an external periphery of the first end of said rod;
   a piston positioned within said cylinder housing between said needle fixing device and said end extension member, said piston being in frictional contact with the interior surface of said cylinder and having a rearward surface juxtaposed to the forward surface of said end extension member, the rearward surface of said piston and the forward surface of said end extension member being dimensioned and arranged such that said forward and rearward surfaces are mechanically free of engagement when in abutting contact;
   a washer having a central aperture, a front end, a rear end and a peripheral edge, said washer being positioned rearward of said end extension member and forward of said cover, the peripheral edge of said washer being in frictional contact with the interior surface of said cylinder, said central aperture being dimensioned so as to receive said rod such that a portion of said rod positioned forward to said washer is free to reciprocate in a forward to rearward direction with respect to said washer, and said central aperture having a periphery which is less than the external periphery of said end extension member such that said end extension member seals said aperture when said end extension member is placed in contact with said washer.

2. A syringe as recited in claim 1, wherein said end extension member is a flat disk attached to a forwardmost end of said rod, and said flat disk having a planar forward surface.

3. A syringe as recited in claim 2 wherein said piston is a solid, cylindrical body with a planar rear surface.

4. A syringe as recited in claim 1 wherein said cover is integral with said cylinder housing so as to form a unitary housing and cover combination.

5. A syringe as recited in claim 1 wherein said rod is a solid, cylindrical rod.

* * * * *